(12) United States Patent
Gabriel et al.

(10) Patent No.: US 10,941,123 B2
(45) Date of Patent: Mar. 9, 2021

(54) TRIAZINE PRECONDENSATE AND METHOD FOR OBTAINING THE SAME

(71) Applicant: Borealis Agrolinz Melamine GmbH, Linz (AT)

(72) Inventors: Herbert Gabriel, Marienkirchen (AT); René Dicke, Leonding (AT); Helmut Puchinger, Freistadt (AT)

(73) Assignee: Borealis Agrolinz Melamine GmbH, Linz (DE)

( * ) Notice: Subject to any disclaimer, the term of this patent is extended or adjusted under 35 U.S.C. 154(b) by 0 days.

(21) Appl. No.: 16/308,645

(22) PCT Filed: Jun. 21, 2017

(86) PCT No.: PCT/EP2017/065242
§ 371 (c)(1),
(2) Date: Dec. 10, 2018

(87) PCT Pub. No.: WO2018/001825
PCT Pub. Date: Jan. 4, 2018

(65) Prior Publication Data
US 2019/0270714 A1    Sep. 5, 2019

(30) Foreign Application Priority Data

Jun. 29, 2016 (EP) .................................... 16176878

(51) Int. Cl.
*C07D 251/70* (2006.01)
*B01J 31/20* (2006.01)

(52) U.S. Cl.
CPC ............ *C07D 251/70* (2013.01); *B01J 31/20* (2013.01)

(58) Field of Classification Search
CPC .................................................. C07D 251/70
USPC ....................................................... 544/198
See application file for complete search history.

(56) References Cited

U.S. PATENT DOCUMENTS

| | | |
|---|---|---|
| 2,358,276 A | 9/1944 | Hodgins et al. |
| 2,544,071 A | 3/1951 | Dudley et al. |
| 3,250,708 A | 5/1966 | Dazzi et al. |
| 3,372,131 A | 3/1968 | Rohlfs et al. |
| 3,730,828 A | 5/1973 | Meiser |
| 4,574,154 A | 3/1986 | Okamoto et al. |
| 4,713,299 A | 12/1987 | Taylor et al. |
| 5,216,156 A | 6/1993 | Galbo et al. |
| 5,306,783 A | 4/1994 | Kirchgaessner et al. |
| 5,330,846 A | 7/1994 | Eisele et al. |
| 5,670,572 A | 9/1997 | Ott et al. |
| 5,792,867 A | 8/1998 | Tanaka et al. |
| 6,001,925 A | 12/1999 | Gapud et al. |
| 6,077,614 A | 6/2000 | Conti et al. |
| 6,307,046 B1 | 10/2001 | Tanaka et al. |
| 6,458,748 B1 | 10/2002 | Yoshimura et al. |
| 8,217,170 B2 | 7/2012 | Sala |
| 8,802,848 B2 | 8/2014 | Dicke et al. |
| 9,546,261 B2 | 1/2017 | Dicke et al. |
| 2006/0051606 A1 | 3/2006 | Decher et al. |
| 2006/0252909 A1 | 11/2006 | Pfeiffer et al. |
| 2006/0276581 A1 | 12/2006 | Ratzsch et al. |
| 2007/0172687 A1 | 7/2007 | Martin-Portugues et al. |
| 2011/0105654 A1 | 5/2011 | Dicke et al. |
| 2011/0178212 A1 | 7/2011 | Dicke et al. |
| 2011/0230586 A1 | 9/2011 | Schwalm et al. |
| 2012/0247559 A1 | 10/2012 | Nakamura et al. |

FOREIGN PATENT DOCUMENTS

| | | |
|---|---|---|
| BE | 619876 A | 1/1963 |
| CA | 773096 A | 5/1967 |
| DE | 3700344 A1 | 4/1988 |
| DE | 3837965 A1 | 5/1990 |
| DE | 4129326 A1 | 3/1993 |
| DE | 4139961 A1 | 6/1993 |
| DE | 10301901 A1 | 7/2004 |
| DE | 102008016966 A1 | 10/2009 |
| EP | 0194080 A2 | 9/1986 |
| EP | 0268809 B1 | 9/1990 |

(Continued)

OTHER PUBLICATIONS

Beyer et al. Chemische Berichte (1966), 99(7), 2123-6.*
Patel et al. International Journal of Chemical Sciences (2014), 12(2), 353-365.*
Santer et al., "Etherified Amino Resins: Synthesis and Reactions in Surface Coatings Applications," Progress in Organic Coatings, 1984, pp. 309-320, vol. 12, Elsevier Sequoia, Netherlands.
Shechter et al., "Glycidyl Ether Reactions with Amines," Industrial and Engineering Chemistry, Jan. 1956, pp. 94-97, vol. 48 No. 1.
Shinoda et al., "Shape-selective N-alkylation of melamine using alcohol as an alkylating agent with Ru/mordenite catalyst in the liquid phase," Studies in Surface Science and Catalysis, 2000, pp. 3465-3470, vol. 130, Elsevier Science B.V.

(Continued)

*Primary Examiner* — Kahsay Habte
(74) *Attorney, Agent, or Firm* — The Webb Law Firm

(57) ABSTRACT

The present invention relates to a triazine precondensate according to the general formula (I) where $R_1$ means $Q^1$ or a moiety of the formula $R_3$—N—$R_4$ connected with the nitrogen atom to the triazine ring of the structure of formula (I), where $R_9$ means $Q^1$ or a moiety of the formula $R_7$—N—$R_8$ connected with the nitrogen atom to the triazine ring of the structure of formula (I), where $R_2$, $R_3$, $R_4$ and $R_6$ mean independently from each other H, $Q^1$ or (i), $R_7$ and $R_8$ mean independently from each other H, $Q^1$, (ii) or (iii) or (i), $R_{10}$ and $R_{11}$ mean independently from each other $R_7$ or $R_8$; $R_5$ means linear or branched $C_2$-$C_{20}$-alkyl that can be interrupted by one or more oxygen atoms, sulphur atoms, substituted or non-substituted nitrogen atoms.

12 Claims, No Drawings

(56) References Cited

FOREIGN PATENT DOCUMENTS

| | | | |
|---|---|---|---|
| EP | 415371 A2 * | 3/1991 | |
| EP | 0710682 A2 | 5/1996 | |
| EP | 0711760 A1 | 5/1996 | |
| EP | 1057821 A1 | 12/2000 | |
| EP | 1247837 B1 | 5/2008 | |
| EP | 2332926 A1 | 6/2011 | |
| EP | 2743282 A1 | 6/2014 | |
| JP | 2000063360 A | 2/2000 | |
| JP | 2004268500 A | 9/2004 | |
| JP | 2006231768 A | 9/2006 | |
| JP | 2008056866 A | 3/2008 | |
| RU | 2337928 C2 | 11/2008 | |
| RU | 2014113461 A | 12/2015 | |
| SU | 66303 A1 | 11/1945 | |
| WO | 9630422 A1 | 10/1996 | |
| WO | 9802474 A1 | 1/1998 | |
| WO | 2005118718 A1 | 12/2005 | |
| WO | 2007012617 A1 | 2/2007 | |
| WO | 2008061923 A1 | 5/2008 | |
| WO | 2009121603 A1 | 10/2009 | |
| WO | 2009121607 A1 | 10/2009 | |
| WO | 2011015539 A1 | 2/2011 | |
| WO | 2013041592 A1 | 3/2013 | |

OTHER PUBLICATIONS

Kreutzberger, "Reactions of Trichloromethyl-1,3,5-triazine Derivatives with Amines", Journal of the American Chemical Society, 1957, pp. 2629-2633, vol. 79, No. 10.

Xiuxiu, L. et al, "Facile Synthesis of Dendritic Hydroxyl-terminated Cyanuric Chloride Derivatives and Their Properties", Chinese Journal of Chemistry, 2012, pp. 1485-1489, vol. 30(7), SIOC, CAS, Shanghai & Wiley-VCH Berlag GmbH & Co. KGaA, Weinheim.

* cited by examiner

TRIAZINE PRECONDENSATE AND METHOD FOR OBTAINING THE SAME

CROSS-REFERENCE TO RELATED APPLICATIONS

This application is the United States national phase of International Application No. PCT/EP2017/065242 filed Jun. 21, 2017, and claims priority to European Patent Application No. 16176878.3 filed Jun. 29, 2016, the disclosures of which are hereby incorporated in their entirety by reference.

BACKGROUND OF THE INVENTION

Field of the Invention

The present invention relates to triazine precondensate and a method for obtaining the same.

Description of the Related Art

Several methods and processes for alkylation of triazines, in particular melamine, have been described.

For example, EP 0 711 760 A1 describes an alkylation of melamine by reacting melamine in the presence of a catalyst and an atmosphere of argon, nitrogen, carbon monoxide or a mixture of hydrogen and carbon monoxide. No complete conversion of the educts and no selectivity in respect to single products are achieved.

EP 1 057 821 A1 describes the alkylation of melamine with alcohols in the presence of metal catalysts with acidic carriers and a nitrogen or hydrogen atmosphere. No complete conversion of the educts and no selectivity in respect to single products are achieved.

JP 2000-063360 A describes a method for alkylation of melamine in which melamine is reacted with an alcohol at high temperatures in the presence of a metal catalyst on a microporous carrier. Thereby, preferably lower alkylated products are obtained.

However, the above methods provide singular modified triazine molecules, but no condensation products thereof.

Typically triazine condensation products are obtained by reaction of a triazine, in particular melamine, and formaldehyde. However, said condensation products, such as Melamine-Formaldehyde-resin, do release the carcinogenic formaldehyde. A reduction of any formaldehyde release from products made of melamine-formaldehyde resin or even a replacement of the formaldehyde by other non-carcinogenic compounds is thus desirable.

SUMMARY OF THE INVENTION

It was thus an object of the present invention to provide novel triazine precondensates which are based on alkylated triazine units, in particular melamine, but are free of formaldehyde.

This object is being solved by a triazine precondensate WITH features as described herein and a method for obtaining the same.

Accordingly, a triazine precondensate according to the general formula (I)

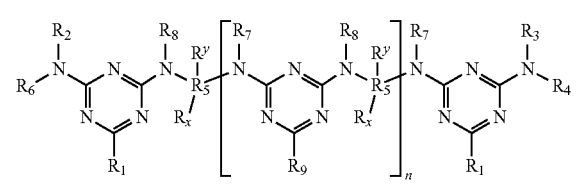

(I)

is provided, wherein $R_1$ means $Q^1$ or a moiety of the formula $R_3$—N—$R_4$ connected with the nitrogen atom to the triazine ring of the structure of formula (I), $R_9$ means $Q^1$ or a moiety of the formula $R_7$—N—$R_8$ connected with the nitrogen atom to the triazine ring of the structure of formula (I), $R_2$, $R_3$, $R_4$ and $R_6$ mean independently from each other H, $Q^1$ or

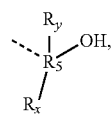

$R_7$ and $R_8$ mean independently from each other H, $Q^1$,

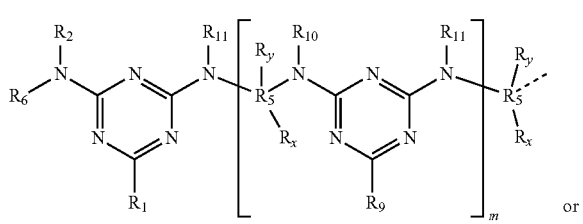

or

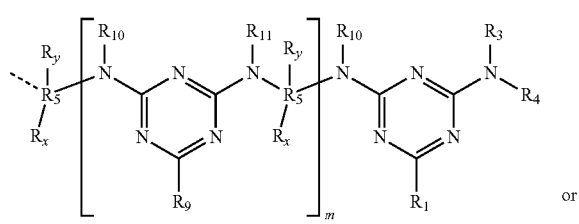

or

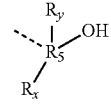

$R_{10}$ and $R_{11}$ mean independently from each other $R_7$ or $R_8$;

$R_5$ means linear or branched $C_2$-$C_{20}$-alkyl that can be interrupted by one or more oxygen atoms, sulphur atoms, substituted and non-substituted nitrogen atoms;

$R_x$, $R_y$ mean independently from each other H, OH, $Q^1$, —[$C_1$-$C_{18}$]—OH or

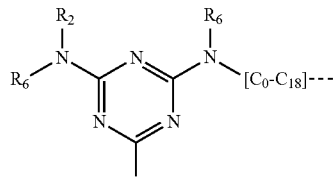

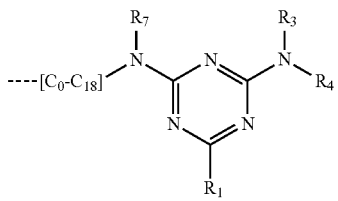

wherein $Q^1$ means linear or branched $C_1$-$C_{20}$-alkyl, linear or branched $C_2$-$C_{20}$-alkenyl, linear or branched $C_2$-$C_{20}$-alkinyl, $C_3$-$C_{10}$-cycloalkyl, $C_5$-$C_7$-cycloalkenyl, $C_6$-$C_{12}$ aryl, which in each case can be interrupted by one or more oxygen atoms, sulphur atoms, and/or by one or more groups of the type —C(O)O—, —OC(O)—, —C(O)—, —NHC(O)O—, —OC(O)NH— and/or —OC(O)O—; and wherein n=0-10, preferably 1-8, most preferably 1-5;

m=0-8, preferably 1-7, most preferably 1-5;

or mixtures thereof.

Thus, a triazine precondensate is provided, wherein two or multiple triazine units are connected to each other. It is to be understood that the structure of the present precondensate may be linear or branched as defined by the different substituents. However, the number of triazine units and thus the length of the condensate is restricted such that the compound is still water soluble.

The present triazine precondensate is obtained in a reaction without using formaldehyde. Rather, the present precondensate is obtained by alkylation with a diol as described in detail below. Therefore the present precondensate does not comprise any methylene linker between two triazine units and does not release any formaldehyde.

Furthermore, the present triazine precondensates are solids that are rather stable at temperatures up to 100-150° C., i.e. the present solid precondensates do not undergo any further reaction, in particular any further hardening reaction without any additional catalyst (i.e. auto-catalytically). The present precondensates are thus more stable in comparison to conventional triazine formaldehdye precondensates that typically undergo a rapid hardening process and can thus not be stored over a longer period of time.

It is also to be understood that a triazine dimer (i.e. n=0) with $R_5$ being —$C_2H_4$— as depicted below is exempted from the presently claimed precondensates:

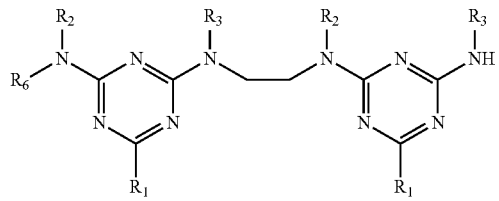

In an embodiment of the present precondensate the moiety $Q^1$ is a linear or branched $C_1$-$C_{12}$-alkyl, $C_3$-$C_7$-cycloalkyl and linear or branched $C_2$-$C_{12}$-alkenyl.

In a further embodiment of the present precondensate the moiety $Q^1$ is a linear or branched $C_1$-$C_6$ alkyl, preferably a $C_2$, $C_3$ or $C_4$ alkyl. $Q^1$ can be for example a methyl, ethyl, n-propyl, isopropyl, n-butyl, s-butyl, t-butyl, isobutyl, pentyl, cyclopentyl, hexyl, cyclohexyl, 2-ethyl-hexyl, octyl, decyl, stearyl, hydroxyethyl, hydroxypropyl or hydroxybutyl. $Q^1$ may be also C6 aryl, in particular phenyl, toloyl, xyloyl.

In an embodiment of the present precondensate the moiety $R_5$ is a linear or branched $C_2$-$C_{20}$ alkyl, preferably a linear or branched $C_2$-$C_{10}$ alkyl, more preferably a linear or branched $C_3$-$C_6$ alkyl.

It is furthermore preferred if the moieties $R_x$, $R_y$ are H, OH, linear or branched $C_1$-$C_{10}$ alkyl, preferably linear or branched $C_2$-$C_6$, or linear or branched [$C_1$-$C_{10}$]—OH, preferably linear or branched [$C_2$-$C_6$]—OH.

In a preferred embodiment of the present precondensate the moieties $R_2$, $R_3$, $R_4$, $R_6$, $R_7$ and $R_8$ are a $C_1$-$C_6$ alkyl comprising in one or more cases at least one OH substituent, in particular a hydroxybutyl.

In a most preferred embodiment of the present precondensate the moieties $R_2$, $R_3$, $R_4$, $R_6$, $R_7$ and $R_8$ are in each case H and $R_5$ is a $C_3$-$C_6$ alkyl, in particular non-substituted —$C_3H_6$—, —$C_4H_8$—, —$C_5H_{10}$— or —$C_6H_{12}$— moiety.

In yet a further variant the present precondensate comprises two, three or four triazine rings wherein at least one of the moieties $R_2$, $R_3$, $R_4$, $R_6$, $R_7$ and $R_8$ is a $C_4$-$C_6$ alkyl comprising in one or more cases at least one OH substituent or a double bond. $R_5$ is a $C_3$-$C_6$ alkyl, in particular non-substituted —$C_3H_6$—, —$C_4H_8$—, —$C_5H_{10}$— or —$C_6H_{12}$— moiety.

It is also possible that a precondensate of two or three triazine rings may comprise only one of the moieties $R_2$, $R_3$, $R_4$, $R_6$, $R_7$ and $R_8$ that are not H. Thus, the alkyl moiety (i.e. $R_2$, $R_3$, $R_4$, $R_6$), in particular a $C_4$-$C_6$ alkyl moiety, preferably with an OH substituent, can be arranged as a terminal moiety on the triazine ring or the alkyl moiety (i.e. $R_7$ and $R_8$) is provided as an internal moiety within the precondensate.

In it is also conceivable that some of the moieties will undergo a cyclization reaction. For example, moieties $R_2$ and $R_6$, $R_3$ and $R_4$ can form a cycloalkyl or heterocycloalkyl ring, respectively. It is also conceivable that moieties $R_7$ and $R_8$ may undergo a cyclization reaction with one of the moieties $R_x$ and $R_y$. It is to be understood that any cyclization reaction depends on the chain length of any of said moieties and possible further substituents enabling ring cyclization such as OH or $NH_2$-moieties.

In case the moieties $R_2$ and $R_6$ and/or $R_3$ and $R_4$ form a cycloylalkyl or heterocycloalkyl ring said ring may be a $C_5$-$C_6$-cycloalkyl, pyrrolidin, morpholine, tetrahydrofuran, piperidin, tetrahydropyran that may be further substituted.

The moieties, in particular $Q^1$ and $R_5$, can be further substituted. Here the term "substituted", in particular in connection to alkyl, alkenyl, alkinyl, cycloalkyl, cycloalkenyl relates to the substitution of one or more atoms, usually H-atoms, by one or more of the following substituents: halogen, hydroxy, protected hydroxy, oxo, protected oxo, $C_3$-$C_7$-cycloalkyl, phenyl, naphthyl, amino, protected amino, primary or secondary amino, heterocyclic ring, imidazolyl, indolyl, pyrrolidinyl, $C_1$-$C_{12}$-alkoxy, $C_1$-$C_{12}$-acyl, $C_1$-$C_{12}$-acyloxy, nitro, carboxy, carbamoyl, carboxamid, N—($C_1$-$C_{12}$-alkyl)carboxamid, N,N-Di($C_1$-$C_{12}$-alkyl)carboxamid, cyano, methylsulfonylamino, thiol, $C_1$-$C_{10}$-alkylthio und $C_1$-$C_{10}$-alkylsulfonyl. The substituted groups can be once or twice substituted with same or different substituents.

Examples for the above substituted alkyl groups comprise 2-oxo-prop-1-yl, 3-oxo-but-1-yl, cyanomethyl, nitromethyl, chlormethyl, hydroxymethyl, tetrahydropyranyloxymethy, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chlormethyl, brommethyl, iodmethyl, trifluormethyl, 6-hydroxyhexyl, 2,4-dichlor(n-butyl), 2-aminopropyl, 1-chlorethyl, 2-chlorethyl, 1-bromethyl, 2-bromethyl, 1-fluorethyl, 2-fluorethyl, 1-iodethyl, 2-iodethyl, 1-chlorpropyl, 2-chlorpropyl, 3-chlorpropyl, 1-brompropyl, 2-brompropyl, 3-brompropyl, 1-fluorpropyl, 2-fluorptopyl, 3-fluorpropyl, 1-iodpropyl, 2-iodpropyl, 3-iodpropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and alike.

Examples for the above substituted alkenyl groups comprise styrolyl, 3-chlor-propen-1-yl, 3-chlor-buten-1-yl, 3-methoxy-propen-2-yl, 3-phenyl-buten-2-yl, 1-cyano-buten-3-yl and alike.

The term "alkinyl" as used herein relates to a moiety of the formulae R—C≡C—, in particular to a $C_2$-$C_{50}$-Alkinyl". Examples for $C_2$-$C_{50}$-alkinyle comprise ethinyl, propinyl, 2-butinyl, 2-pentinyl, 3-pentinyl, 2-hexinyl, 3-hexinyl, 4-hexinyl, 2-heptinyl, 3-heptinyl, 4-heptinyl, 5-heptinyl, octinyl, noninyl, decinyl, undecinyl, dodecinyl, as well as di- and tri-ines of straight or branched alkyl chains.

The term "$C_1$-$C_{12}$-alkyl" relates to moieties like methyl, ethyl, n-propyl, isopropyl, n-butyl, isobutyl, s-butyl, t-butyl, amyl, t-amyl, hexyl, heptyl, octyl, nonyl, decyl, undecyl, dodecyl, and alike. Prefererd $C_1$-$C_{12}$-alkyl groups are methyl, ethyl, isobutyl, s-butyl und isopropyl.

The term "oxo" relates to a carbon atom, which is connected with an oxygen atom via a double bond whereby a keto or an aldehyde group is formed. The term "protected oxo" relates to a carbon atom, which is substituted by two alkoxy groups or is connected twice with a substituted diol forming a non-cyclic or cyclic ketal group.

The term "alkoxy" relates to moieties like methoxy, ethoxy, n-propoxy, isopropoxy, n-butoxy, t-butoxy and alike. A preferred alkoxy group is methoxy.

The term "$C_3$-$C_7$-cycloalkyl" comprises groups like cyclopropyl, cyclobutyl, cyclopentyl, cyclohexyl und cycloheptyl. The term "$C_5$-$C_7$-Cycloalkenyl" relates to a 1,2 oder 3-cyclopentenyl ring, a 1,2,3 or 4-cyclohexenyl ring or a 1,2,3,4 or 5-cycloheptenylring.

In a preferred embodiment of the present invention the compounds have one of the following structures:

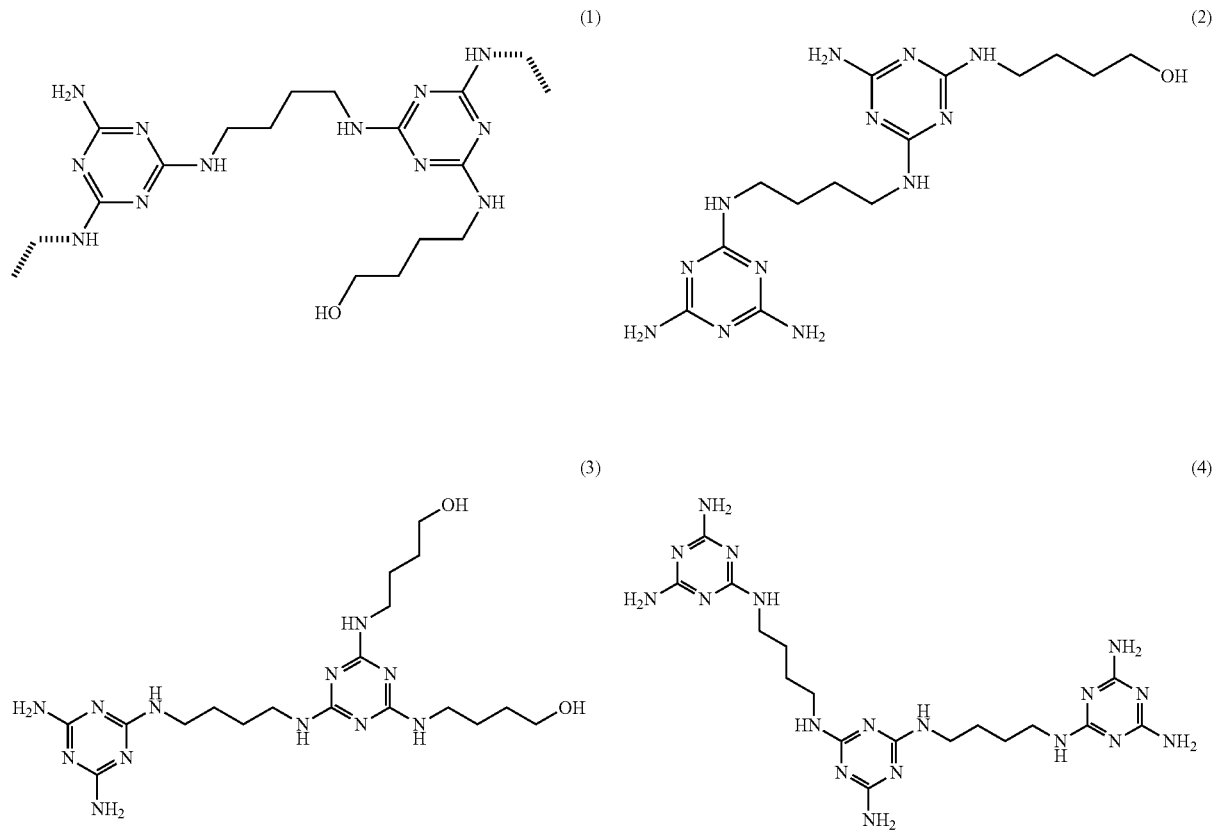

(5)
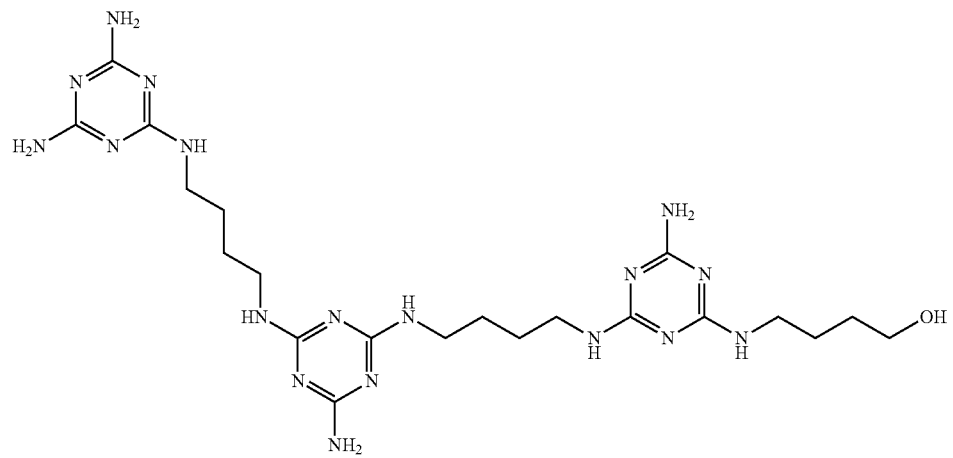
(6)
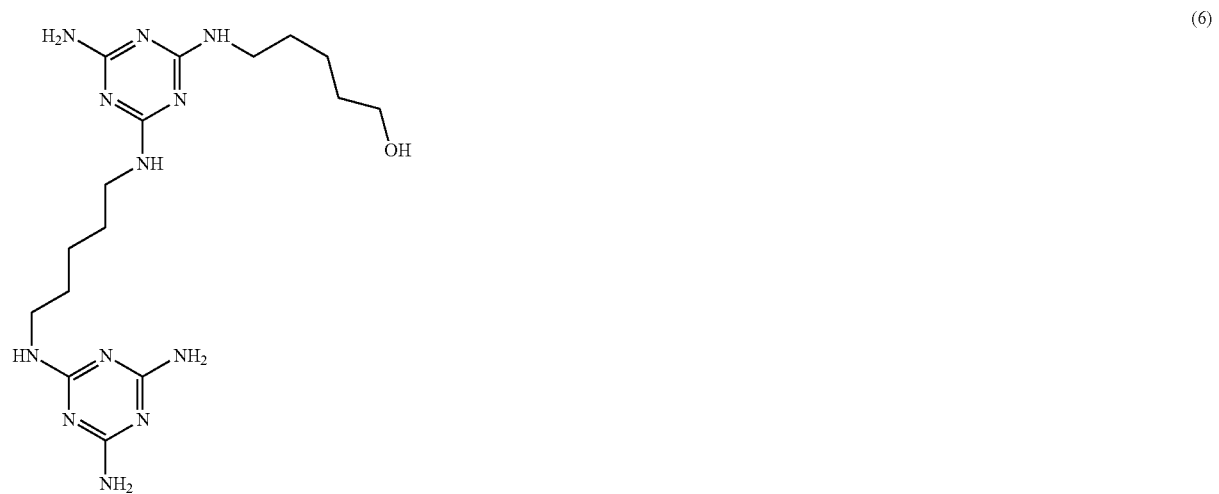
(7)
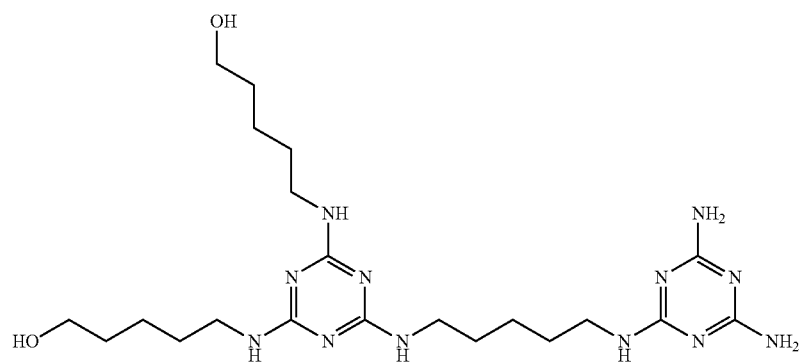

-continued
(8)
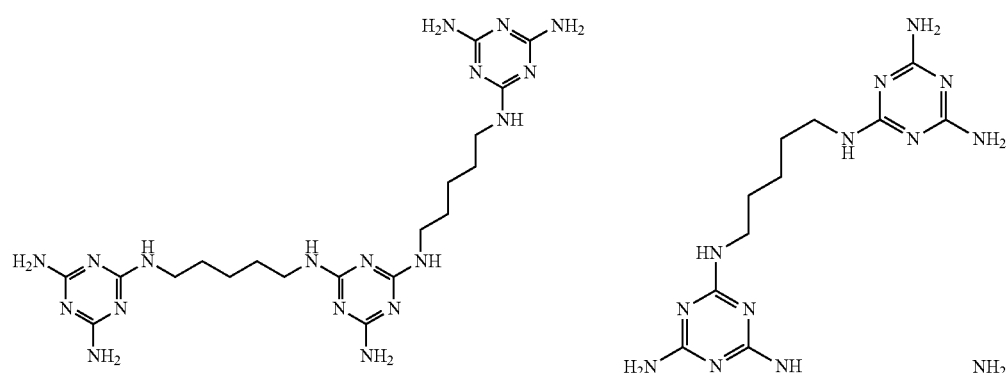
(9)
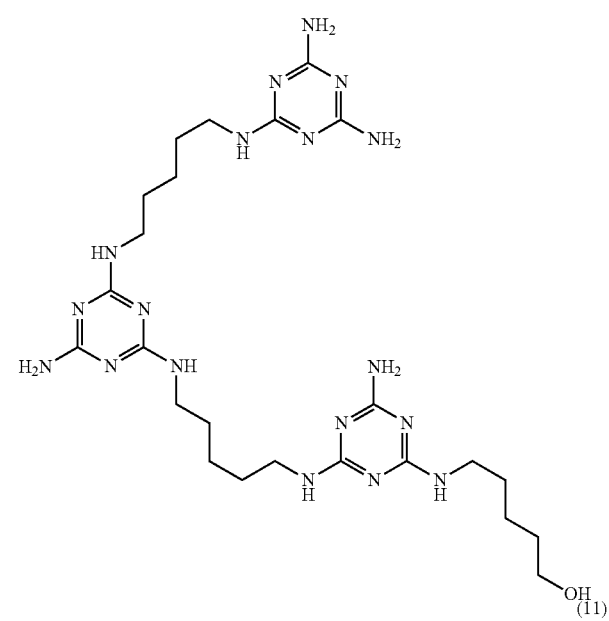
(10)
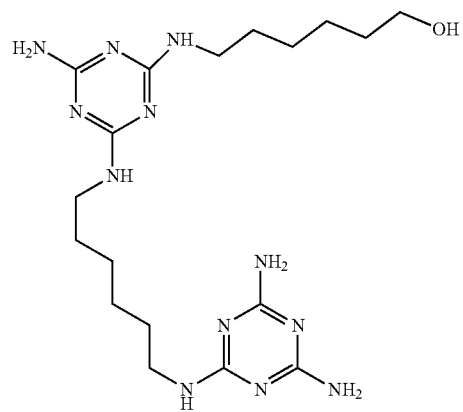
(11)
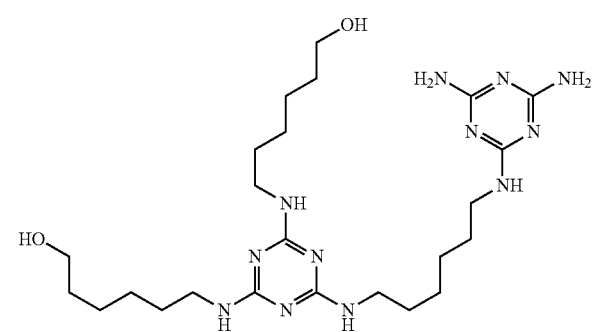
(12)
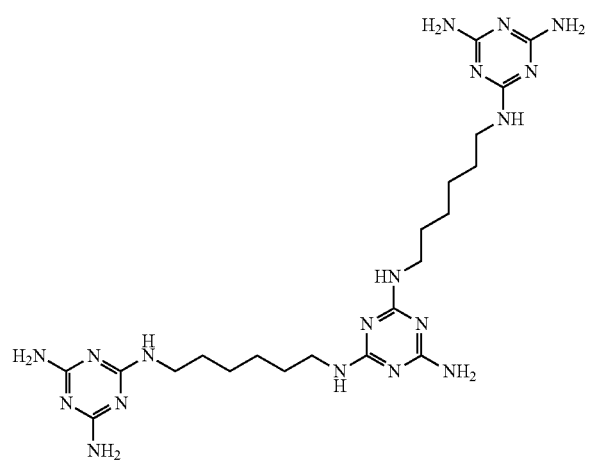
(13)
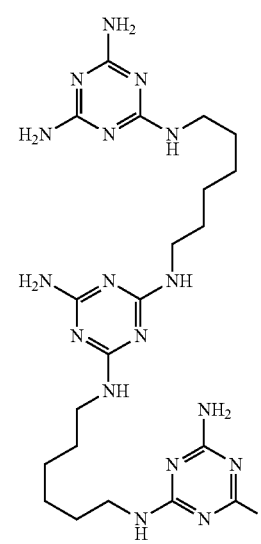

-continued (14)

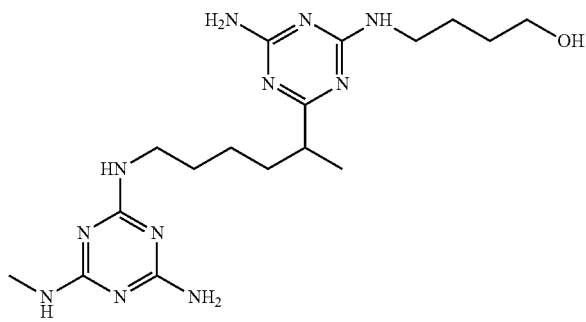

(15)

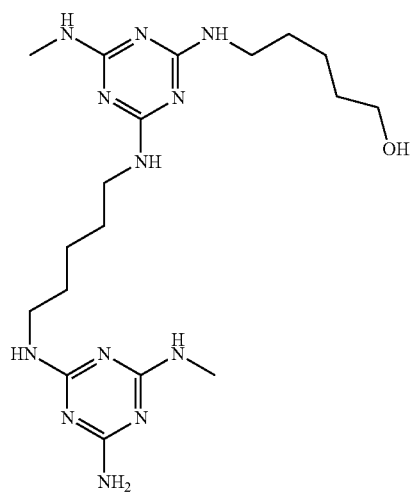

(16)

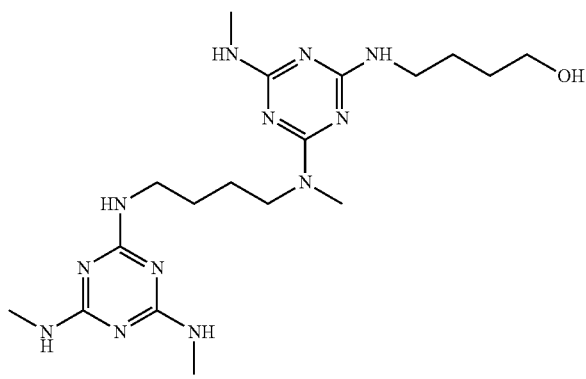

The present triazine precondensate has a melting range between 50 and 300° C. that is depending on the substitutional pattern of the triazine ring. The same is valid for the water solubility of the present precondensate that depends primarily on number of free OH groups in the precondensate.

The present triazine precondensate is obtained in a method, wherein
at least one triazine of the general formula (II)

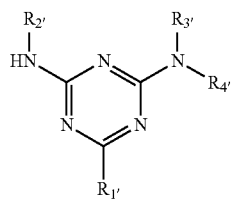

and at least one alcohol of the general formula (III)

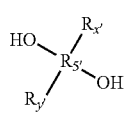

(III)

or a mixture of at least one alcohol of general formula (III) and general formula (IV)

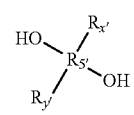

(III)

(IV)

wherein $R_1'$, $R_2'$, $R_3'$, $R_4'$, $R_5'$, $R_6'$, $R_x'$ and $R_y'$ have the meanings of $R_1$, $R_2$, $R_3$, $R_4$, $R_5$, $R_6$, $R_x$ and $R_y$, are reacted.

It is to be understood that when reacting a triazine of formula (II) and an alcohol of formula (III) optionally together with an alcohol of formula (IV) a reaction mixture is obtained that comprises triazine precondensates in form of dimers, trimers and higher oligomers as well as substituted triazine monomers (for example triazine monomers substituted with one alcohol of formula (III) and/or alcohol of formula (IV).

The moiety $R_5'$ in the alcohol of general formula (III) may be a linear or branched $C_2$-$C_{10}$ alkyl, preferably a linear or branched $C_2$-$C_{10}$ alkyl; more preferably a linear or branched $C_3$-$C_6$ alkyl. Thus, alcohol according to general formula (III) can be selected from a group comprising diols, in particular ethandiol, propandiol, butandiol, pentandiol or hexandiol, diethylenglycol, triethanolamine, diethanolamine, triols (such as trimethylol propan) and tetraols (such as pentaerythrit). The alcohol according to general formula (IV) can be any suitable monoalcohol.

The triazine of formula (II) may be preferably selected from a group comprising melamine, acetoguanamine, benzoguanamine or alkylated melamine. Melamine is however the preferred triazine of general formulae (II).

According to the present method the reaction of triazine and alcohol(s) is carried out in the presence of one catalyst selected from a group comprising a metal or metal oxide, wherein the metal is from $8^{th}$, $9^{th}$ or $10^{th}$ group of the periodic system, wherein the one catalyst does not comprise any carrier material.

Thus, in the present method only one metal, metal oxide, metal salt or metal complex catalyst is used that is free of any type of carrier material. Furthermore, no binary catalytic system such as a mixture of two catalysts is used.

In a preferred embodiment the one catalyst does not comprise any acidic carrier material, in particular no zeolithe, alumo silicate, alumo phosphate, metal oxide, silicate, layered silicate, aluminium oxide, silizium dioxide and/or carbon.

In an embodiment the catalyst comprises a metal or metal oxide selected from a group comprising Ru, Rh, Pd, Pt, Co, Fe. In particular a preferred catalyst is selected from the group comprising triruthenium dodecarbonyl, Potassium perruthenate $KRuO_4$, Ruthenium(III) acetylacetonate $(C_5H_7O_2)_3Ru$, Ruthenium(IV) oxide $RuO_2$ sowie Palladium (II) oxide PdO, Hexaamineruthenium(III) chloride [Ru(NH$_3$)$_6$]Cl$_3$, ruthenium(III) nitrosylchloride Cl$_3$NORu, potassium pentachloronitrosylruthenium(II), tetraacetatochlorodiruthenium(II,III), dichlorobis(2,2'-bipyridyl)ruthenium(II), tris(2,2'-bipyridyl)ruthenium(II) chloride, Rhodium(III) nitrate hydrate Rh(NO$_3$)$_3$.xH$_2$O, Rhodium(II) chloride RhCl$_3$, Palladium(II)acetate $C_4H_6O_4Pd$, Palladium(II)acetonylacetate $C_{10}H_{14}O_4Pd$, Palladium(II)chloride PdCl$_2$, Platinum (IV)chloride PtCl$_4$, Platinum(II)chloride PtCl$_2$, Platinum(IV)oxide PtO$_2$, Potassium hexachloroplatinate(IV) Cl$_6$K$_2$Pt, Sodium hexahydroxyplatinate(IV) H$_6$Na$_2$O$_6$Pt, Tetraamineplatinum(III) chloride hydrate H$_{12}$Cl$_2$N$_4$Pt.xH$_2$O, Cobalt(II) acetylacetonate $C_{10}H_{14}CoO_4$, Sodium hexanitrocobaltate(III) CoN$_6$Na$_3$O$_{12}$, Cobalt carbonyl Co$_2$(CO)$_8$, Diironnonacarbonyl Fe$_2$(CO)$_9$, Iron(III) acetylacetonate $C_{15}H_{21}FeO_6$, Triirondodecarbonyl Fe$_3$(CO)$_{12}$, Potassium ferrate(VI) K$_2$FeO$_4$.

The amount of catalyst required in the present method may be between 0.001 to 2 Mass %, preferably 0.01 to 1.5 Mass %, mostly preferably 0.1 to 1 Mass % in respect to the triazine, in particular melamine.

In a further embodiment of the present method the reaction is carried out at a temperature between 80° C. and 300° C., in particular 150° C. and 270° C., in particular 180° C. and 260° C.

In yet another preferred embodiment of the present method the reaction time is at least 2 hours, preferably at least 6 hours. Specifically the reaction time is between 4 and 12 hours, preferably between 5 and 10 hours, most preferably between 6 and 8 hours.

In a mostly preferred embodiment of the present method the molar ratio of the at least one triazine of the general formula (II) and the at least one alcohol of the general formula (III) or the mixture of the at least one alcohol of the general formula (III) and at least one alcohol of the general formula (IV) is between 1:0.3 to 1:3, preferably 1:0.5 to 1:2, mostly preferably 1:0.6 to 1:1.6

When using a mixture of the alcohol of formula (III) and an alcohol of formula (IV) as reaction partner for the triazine of formula (II) the ratio of alcohol of formula (III) and alcohol of formula (IV) may be between 1:0 to 1:2, preferably 1:0 to 1:1.5, most preferably 1:0 to 1:0.8.

A ratio close to equimolar of triazine and alcohol is particularly preferred. When using an equimolar ratio of triazine and alcohol not all amino groups on the triazine ring will react with the alcohol. Thus, the triazine molecules are forced to undergo a reaction with each other thereby forming dimers, trimers and higher oligomers.

The reaction according to the present method is carried out in a pressure range between 1 bar and 100 bar, preferably between 5 bar and 50 bar. The reaction may be started under normal pressure or also at higher pressure of about 5 bar. It is to be understood that the pressure may increase in the course of the reaction in conjunction with a temperature increase.

The present method may be carried out in a hydrogen gas atmosphere, preferably in a mixture of hydrogen gas and an inert gas such as nitrogen, argon or helium.

The present method enables the formation of longer linked bridges between triazine units in comparison to the conventionally used formaldehyde.

The difference between both reaction types are shown below. Here a comparison between hydroxymethylation (using formaldehyde) and alkylation (using diols) according to the present method is provided.

Hydroxymethylation:

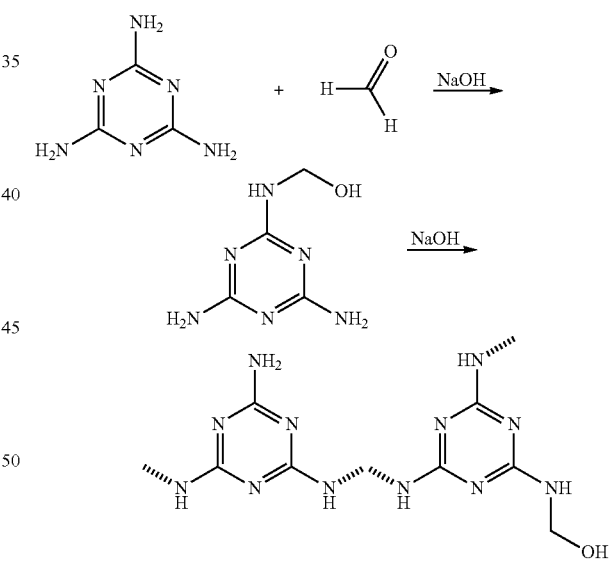

Alkylation according to the present method:

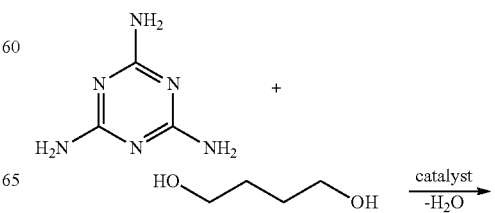

-continued

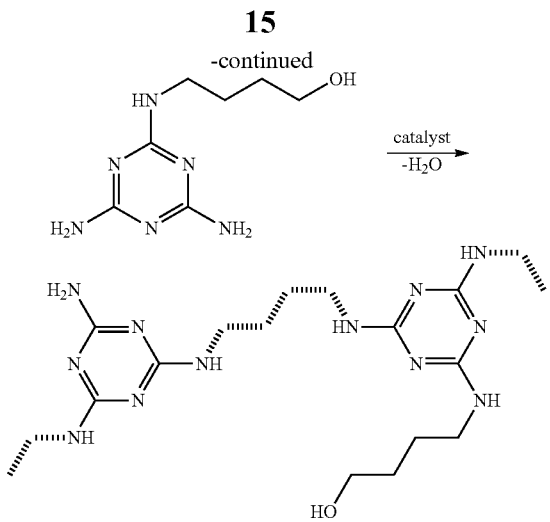

Due to the integration of longer linked bridges, the precondensate is more flexible and free of any formaldehyde. Due to the availability of two or more hydroxy-groups in the polyol (diol, triole or tetraole) as reaction partner, both groups are able to react and a melamine-diol-precondensate is formed that is comparable to the precondensate formation of MF-resins.

DESCRIPTION OF THE INVENTION

The invention is explained in more detail by means of the following examples.

Example 1: Comparative Example 2.5 g melamine, 105 g 1.4 butanediol and 0.5 g Ru/Al$_2$O$_3$ catalyst were mixed in a beaker and filled into the autoclave. The autoclave was closed and the stirrer was turned on with 500 rpm. After flushing with helium, hydrogen was flushed through the autoclave and then it was closed with atmospheric pressure of hydrogen inside. The reaction mixture was heated up to 250° C. and held at this temperature for 6 hours. After cooling down to room temperature and flushing with helium the autoclave was opened and the reaction mixture was transferred into a beaker. The catalyst was separated with a centrifuge. The reaction product was precipitated in a mixture of acetone and water (1:1). The product was filtered and dried in a vacuum drying chamber and analysed with HPLC. The reaction products are monomers.

Example 2: Inventive Example 70 g melamine, 100 g 1,4-butanediol and 1 g triruthenium dodecarbonyl were mixed in a beaker and filled into the autoclave. The autoclave was closed and the stirrer was turned on with 500 rpm. After flushing with helium, hydrogen was flushed through the autoclaved and then it was closed with atmospheric pressure of hydrogen inside. The reaction mixture was heated up to 250° C. and held at this temperature for 6 hours. After cooling down to room temperature and flushing with helium the autoclave was opened and the reaction mixture was transferred into a beaker. The reaction product was dissolved in 500 ml acetone-water (7:1). The catalyst was separated with a centrifuge and the solvent (water) was evaporated in a Rotavapor. The residue was dried in a vacuum drying chamber and analysed with HPLC. The reaction product was washed with acetone, filtered and analysed with HPLC. The solvent of the filtrate was evaporated with the Rotavapor and the residue was analysed by HPLC. The product has a yield of precondensate with minimum 2 triazine units of >90%. The product is water soluble.

Tables 1 and 2 depict determined structures of the reaction according to Example 2. It is to be noted that the side chain formed from butanediol may also undergo a cyclization forming a pyrrolidin moiety. Table 1 depicts the monomeric structures wherein their percentage is below 10%. Table 2 depicts the structures of the present precondensate products comprising preferably 2-3 triazine.

TABLE 1

| Structure (Examples) | | Molecular weight [g/mol] | Retention Time [min] |
|---|---|---|---|
| 1 Triazine unit 1 Alcohol unit | 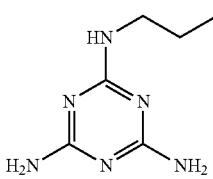 Molecular Weight: 198.23 | 198.23 | 1.2 |
|  | 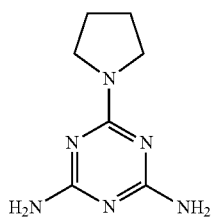 [SMILES: Nc1nc(N)nc(N2CCCC2)n1] Molecular Weight: 180.22 | 180.22 | 2.9 |
| 1 Triazine unit 2 alcohol units | 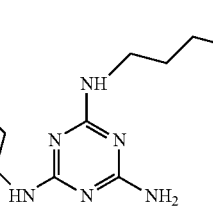 Molecular Weight: 270.34 | 270.34 | 2.2 |
|  | 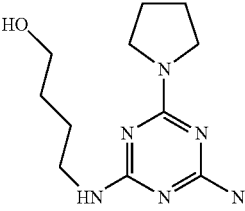 Molecular Weight: 252.32 | 252.32 | 7.8 |

TABLE 2
| Structure (Examples) | Molecular weight [g/mol] | Retention Time [min] |
|---|---|---|
| 2 Triazine units<br>1 Alcohol unit 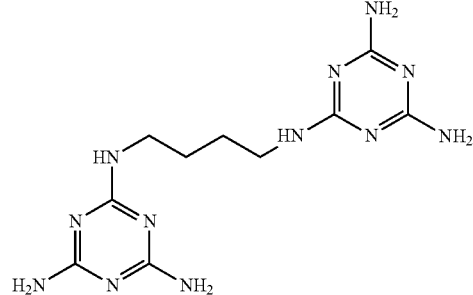 [SMILES: Nc1nc(N)nc(NCCCCNc2nc(N)nc(N)n2)n1]<br>Molecular Weight: 306.34 | 306.34 | 1.8 |
| 2 Triazine units<br>2 Alcohol units 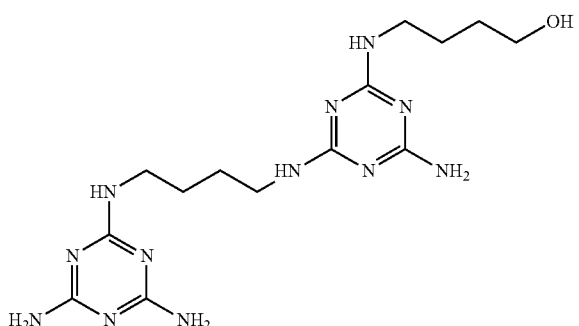<br>Molecular Weight: 378.45 | 378.45 | 3.8 |
| 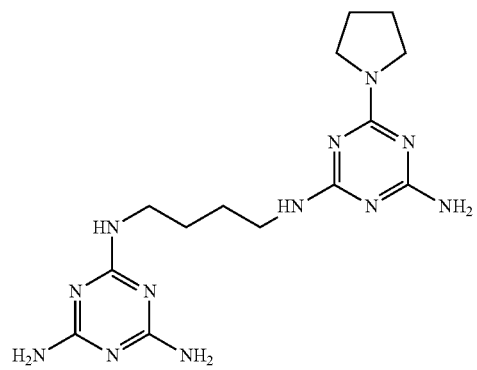 [SMILES: Nc1nc(N)nc(NCCCCNc2nc(N)nc(N3CCCC3)n2)n1]<br>Molecular Weight: 360.43 | 360.43 | 8.4 |
| 2 Triazine units<br>3 Alcohol units 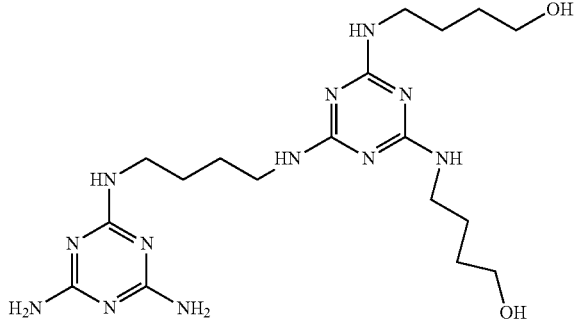 [SMILES: Nc1nc(N)nc(NCCCCNc2nc(NCCCCO)nc(NCCCCO)n2)n1]<br>Molecular Weight: 450.55 | 450.55 | |

TABLE 2-continued
| Structure (Examples) | Molecular weight [g/mol] | Retention Time [min] |
|---|---|---|
| 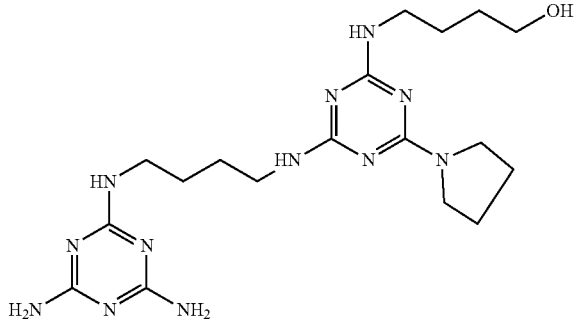 [SMILES: Nc1nc(N)nc(NCCCCNc2nc(NCCCCO)nc(N3CCCC3)n2)n1]<br>Molecular Weight: 432.54 | 432.54 | 9.4 |
| 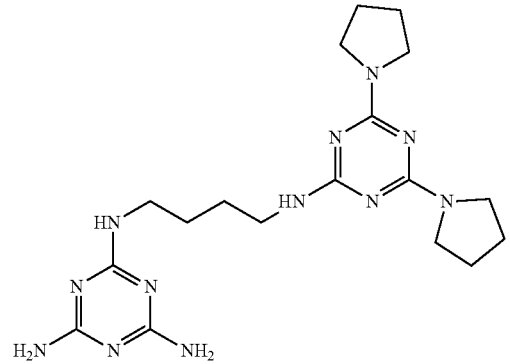 [SMILES: Nc1nc(N)nc(NCCCCNc2nc(N3CCCC3)nc(N3CCCC3)n2)n1]<br>Molecular Weight: 414.52 | 414.52 | 11.5 |
| 3 Triazine units<br>2 Alkohol units<br>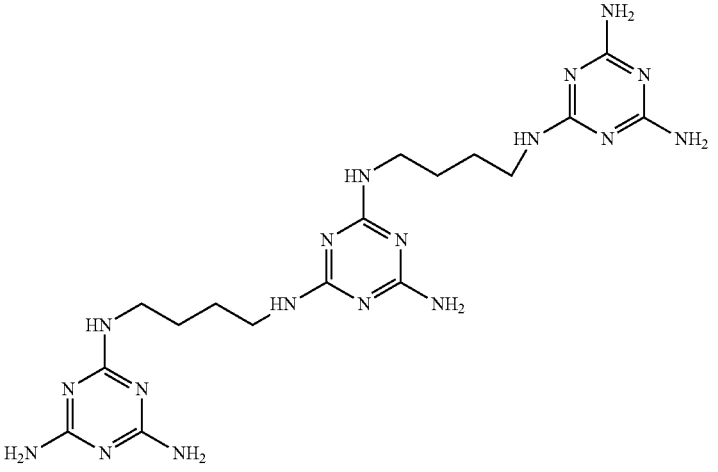 [SMILES: Nc1nc(N)nc(NCCCCNc2nc(N)nc(NCCCCNc3nc(N)nc(N)n3)n2)n1]<br>Molecular Weight: 486.55 | 486.55 | 12.8 |

TABLE 2-continued

| Structure (Examples) | Molecular weight [g/mol] | Retention Time [min] |
|---|---|---|
| 3 Triazine units<br>3 alcohol units 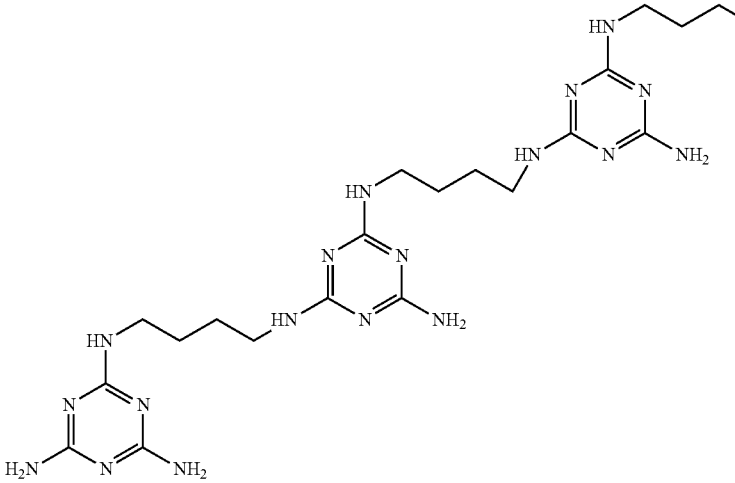<br>Molecular Weight: 558.66 | 558.66 | |
| 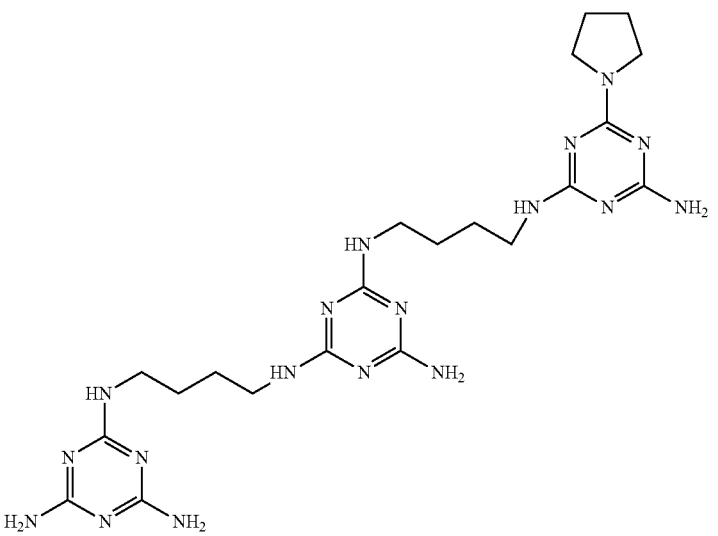 [SMILES: Nc1nc(N)nc(NCCCCNc2nc(N)nc(NCCCCNc3nc(N)nc(N4CCCC4)n3)n2)n1]<br>Molecular Weight: 540.65 | 540.64 | 15.5 |

HPLC-Method:

Column: Purospher® STAR RP-8e (5 μm) LiChroCART® 125-2 HPLC Cartridge

Mobile Phase: A: Water (1 g ammonium formiate+20 μl NH$_4$OH Conc. (25%) per liter)

B: Acetonitril

Gradient:

| Time(min) | % A | % B |
|---|---|---|
| 0 | 90 | 10 |
| 2 | 90 | 10 |
| 24 | 3 | 97 |

-continued

| Time(min) | % A | % B |
|---|---|---|
| 32 | 3 | 97 |
| 32.01 | 90 | 10 |

Temperature: 40° C.

Example 3: Inventive Example 70 g melamine, 100 g 1,4-butanediol and 1 g triiron dodecarbonyl were mixed in a beaker and filled into the autoclave. The autoclave was closed and the stirrer was turned on with 500 rpm. After flushing with helium, hydrogen was flushed through the autoclaved and then it was closed with atmospheric pressure of hydrogen inside. The reaction mixture was heated up to 250° C. and held at this temperature for 6 hours. After cooling down to room temperature and flushing with helium the autoclave was opened and the reaction mixture was transferred into a beaker. The reaction product was dissolved in 500 ml acetone-water (7:1). The catalyst was separated with a centrifuge and the solvent (water) was evaporated in a Rotavapor. The residue was dried in a vacuum drying chamber and analysed with HPLC. The reaction product was washed with acetone, filtered and analysed with HPLC. The solvent of the filtrate was evaporated with the Rotavapor and the residue was analysed by HPLC. The product is water soluble.

Tables 3 and 4 depict determined structures of the reaction according to Example 3. It is to be noted that the side chain formed from butanediol may also undergo a cyclization forming a pyrrolidin moiety. Table 3 depicts the monomeric structures wherein their percentage is below 10%. Table 4 depicts the structures of the present precondensate products comprising preferably 2-3 triazine.

TABLE 3

| Structure (Examples) | | Molecular weight [g/mol] | Retention Time [min] |
|---|---|---|---|
| 1 Triazine unit 1 Alcohol unit | (structure shown) | 198.23 | 1.2 |

Molecular Weight: 198.23

TABLE 3-continued

| Structure (Examples) | | Molecular weight [g/mol] | Retention Time [min] |
|---|---|---|---|
| | (structure shown) | 180.22 | 2.9 |

Molecular Weight: 180.22

| 1 Triazine unit 2 alcohol units | (structure shown) | 270.34 | 2.2 |

Molecular Weight: 270.34

| | (structure shown) | 252.32 | 7.8 |

Molecular Weight: 252.32

TABLE 4

| Structure (Examples) | | Molecular weight [g/mol] | Retention Time [min] |
|---|---|---|---|
| 2 Triazine units 1 Alcohol unit | 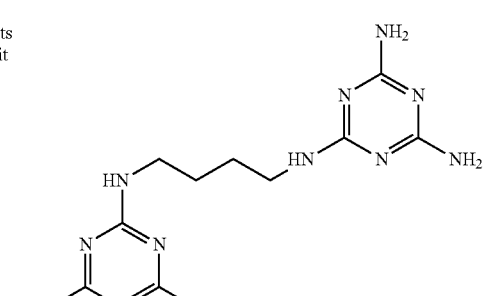 | 306.34 | 1.8 |

Molecular Weight: 306.34

TABLE 4-continued

| Structure (Examples) | Molecular weight [g/mol] | Retention Time [min] |
|---|---|---|
| 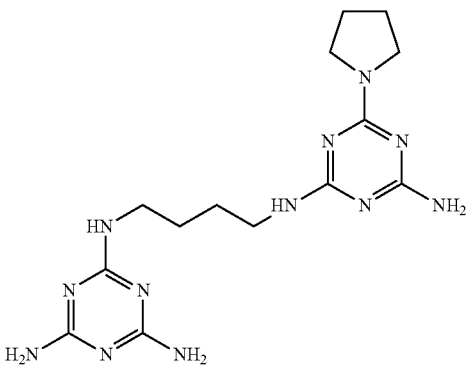 [SMILES: Nc1nc(N)nc(NCCCCNc2nc(N)nc(N3CCCC3)n2)n1]  Molecular Weight: 360.43 | 360.43 | 8.4 |

Hplc-Method:

Column: Purospher® STAR RP-8e (5 μm) LiChroCART® 125-2 HPLC Cartridge

Mobile Phase: A: Water (1 g ammonium formiate+20 μl NH$_4$OH Conc. (25%) per liter)

B: Acetonitril

Gradient:

| Time(min) | % A | % B |
|---|---|---|
| 0 | 90 | 10 |
| 2 | 90 | 10 |
| 24 | 3 | 97 |
| 32 | 3 | 97 |
| 32.01 | 90 | 10 |

Temperature: 40° C.

The invention claimed is:

1. A triazine precondensate according to the general formula (I)

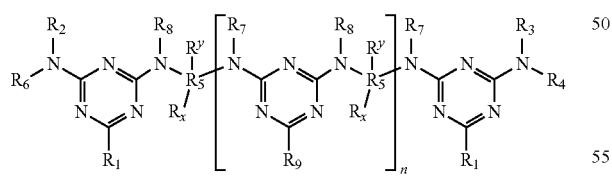

(I)

wherein $R_1$ means $Q^1$ or a moiety of the formula $R_3$—N—$R_4$ connected with the nitrogen atom to the triazine ring of the structure of formula (I), $R_9$ means $Q^1$ or a moiety of the formula $R_7$—N—$R_8$ connected with the nitrogen atom to the triazine ring of the structure of formula (I), $R_2$, $R_3$, $R_4$ and $R_6$ mean independently from each other H or

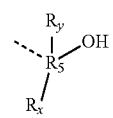

$R_7$ and $R_8$ mean independently from each other H,

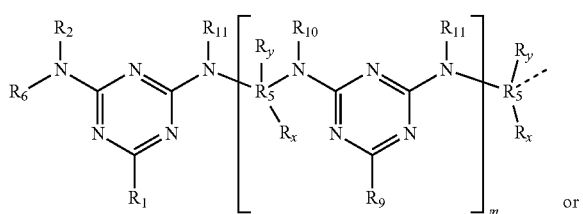

or

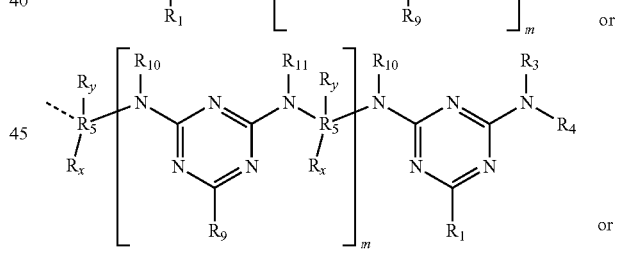

or

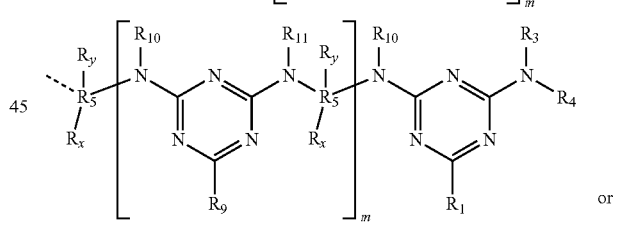

wherein at least one of $R_2$, $R_3$, $R_4$, $R_6$, $R_7$ and $R_8$ is a $C_4$-$C_6$ alkyl comprising at least one OH substituent, with the proviso that when n=0, $R_5$ is not —$C_2H_4$—, $R_{10}$ and $R_{11}$ mean independently from each other $R_7$ or $R_8$;

$R_5$ means linear or branched $C_2$-$C_{20}$-alkyl that can be interrupted by one or more oxygen atoms, sulphur atoms, and/or nitrogen atoms $R_x$, $R_y$ mean independently from each other H, OH, $Q^1$, —[$C_1$-$C_{18}$]—OH or

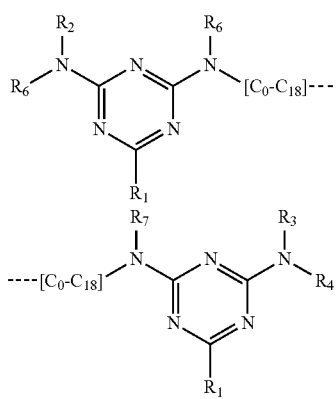

wherein

Q$^1$ means linear or branched $C_1$-$C_{12}$-alkyl, linear or branched $C_2$-$C_{12}$ alkenyl, $C_3$-$C_7$-cycloalkyl, or $C_6$-$C_{12}$ aryl; and wherein n=0-10;
m=0-8;
or mixtures thereof.

2. The triazine precondensate according to claim 1, wherein Q$^1$ is a linear or branched $C_1$-$C_6$ alkyl.

3. The triazine precondensate according to claim 1, wherein the moiety $R_5$ is a linear or branched $C_2$-$C_{10}$ alkyl, and the moieties $R_x$, $R_y$ are H, OH, linear or branched $C_1$-$C_{10}$ alkyl, or linear or branched [$C_1$-$C_{10}$]—OH.

4. The triazine precondensate according to claim 1, wherein the moieties $R_2$, $R_3$, $R_4$, $R_6$, $R_7$ and $R_8$ are in each case H and $R_5$ is a $C_2$-$C_6$ alkyl.

5. The triazine precondensate according to claim 1, comprising a melting range between 50 and 300° C.

6. The triazine precondensate according to claim 1, wherein n=1-5.

7. The triazine precondensate according to claim 1, wherein m=1-5.

8. The triazine precondensate according to claim 2, wherein Q$^1$ is a $C_2$, $C_3$, or $C_4$ alkyl.

9. The triazine precondensate according to claim 3, wherein the moiety $R_5$ is a $C_3$-$C_6$ alkyl.

10. The triazine precondensate according to claim 3, wherein the moieties $R_x$, $R_y$ are H, OH, linear or branched $C_2$-$C_6$ alkyl, or linear or branched [$C_2$-$C_6$]—OH.

11. The triazine precondensate according to claim 1, wherein the precondensate comprises three or four triazine rings.

12. The triazine precondensate according to claim 1, wherein the moiety $R_5$ is a linear or branched $C_3$-$C_6$ alkyl.

* * * * *